United States Patent
Jukarainen et al.

(10) Patent No.: US 6,887,948 B2
(45) Date of Patent: May 3, 2005

(54) METHOD FOR PREPARING A SILOXANE-BASED ELASTOMER COMPOSITION

(75) Inventors: Harri Jukarainen, Turku (FI); Tommi Markkula, Turku (FI); Juha Ala-Sorvari, Turku (FI); Matti Lehtinen, deceased, late of Piispanristi (FI); by Pirkko Lehtinen, legal representative, Piispanristi (FI); Jarkko Ruohonen, Vahalinna (FI)

(73) Assignee: Schering Oy, Turku (FI)

( * ) Notice: Subject to any disclaimer, the term of this patent is extended or adjusted under 35 U.S.C. 154(b) by 0 days.

(21) Appl. No.: 10/298,197

(22) Filed: Nov. 18, 2002

(65) Prior Publication Data

US 2003/0096921 A1 May 22, 2003

Related U.S. Application Data

(63) Continuation-in-part of application No. 09/701,547, filed as application No. PCT/FI99/00511 on Jun. 11, 1999, now abandoned.

(30) Foreign Application Priority Data

Jun. 30, 1998 (FI) ................................................. 981506

(51) Int. Cl.$^7$ .............................................. C08L 83/10
(52) U.S. Cl. ........................ 525/477; 528/24; 524/588; 556/445
(58) Field of Search .......................... 525/477; 528/24; 524/588; 556/445

(56) References Cited

U.S. PATENT DOCUMENTS

| | | | |
|---|---|---|---|
| 3,836,560 A | 9/1974 | Prokai et al. ......... 260/448.8 R |
| 4,391,963 A | * 7/1983 | Shirahata ..................... 528/37 |
| 4,600,751 A | 7/1986 | Lee et al. ................... 525/404 |
| 5,889,108 A | 3/1999 | Zhang ......................... 524/862 |
| 6,013,711 A | 1/2000 | Lewis et al. ................ 524/265 |
| 6,476,079 B1 | 11/2002 | Jukarainen et al. ...... 514/772.4 |
| 2003/0096920 A1 | 5/2003 | Jukarainen et al. ......... 525/474 |

FOREIGN PATENT DOCUMENTS

| | | |
|---|---|---|
| EP | 545 002 | 6/1993 |
| EP | 882 753 | 12/1998 |
| FI | 973 427 | 2/1999 |
| JP | 50-50465 | * 5/1975 |

OTHER PUBLICATIONS

Hans W. Haesslin, et al., "Dimethylsiloxane–ethylene oxide block copolymers, 1, Microphase separation of low segment mass copolymers and their compatibility with water and oil", 185 *Makromol. Chem.* 2625–2645 (1984).

Hans w. Haesslin, "Dimethylsiloxane–ethylene oxide block copolymers 2, Preliminary results on dilute solution properties", 186 *Makromol. Chem.* 357–366 (1985).

Katherine L. Ullman et al, "Drug Permeability of Modified Silicone Polymers I. Silicone–organic Block Copolymers", 10 *J. Controlled Release* 251–260 (1989).

Chemical Abstracts 126: 2000090, "Synthesis and Drug Release Property of Polysiloxane Containing Pendant Long Alkyl Ether Group" (1997).

Meals et al., *Silicones* 115–116 (1959).

Sun et al., "Effect of Polymer Composition on Steroid Permeation: Membrane Permeation Kinetics of Androgens and Progestins," 5 *J. Controlled Release* 69–78 (1987).

* cited by examiner

*Primary Examiner*—Kuo-Liang Peng
(74) *Attorney, Agent, or Firm*—James C. Lydon

(57) ABSTRACT

The invention relates to a method for the preparation of a siloxane-based elastomer composition comprising at least one elastomer, said elastomer composition comprising poly (alkylene oxide) groups present in the elastomer as alkoxy-terminated grafts of polysiloxane units and linked to the polysiloxane units by silicon-carbon bonds wherein at least one vinyl functional polymer component is crosslinked in the presence of a peroxide catalyst.

17 Claims, No Drawings

METHOD FOR PREPARING A SILOXANE-BASED ELASTOMER COMPOSITION

This application is a continuation-in-part of application Ser. No. 09/701,547 filed Nov. 30, 2000, now abandoned, which is a U.S. National Stage of International application PCT/FI99/00511, filed Jun. 11, 1999.

The invention relates to a method for the preparation of a siloxane-based elastomer composition comprising at least one elastomer, said elastomer composition comprising poly(alkylene oxide) groups present in the elastomer as alkoxy-terminated grafts of polysiloxane units and linked to the polysiloxane units by silicon-carbon bonds.

STATE OF THE ART

Polysiloxanes, in particular poly(dimethyl siloxane) (PDMS), are highly suitable for use as a membrane or matrix regulating the permeation rate of drugs in various drug forms, in particular in implants and IU systems. Polysiloxanes are physiologically inert, and a wide group of drugs are capable of penetrating polysiloxane membranes, which also have the required strength properties.

It is known from the literature that the adding of poly(ethylene oxide) groups, i.e. PEO groups, to a PDMS polymer may increase the permeation rate of drugs. Publication K L Ullman et al., Journal of Controlled Release 10 (1989) 251–260, describes membranes prepared from a block copolymer which contains PEO and PDMS and the penetration of various steroids through these membranes. It is noted in the publication that an increasing PEO amount in the block polymer tends to increase the penetration of hydrophilic steroids, while the penetration of lipophilic steroids decreases. The block copolymer described in the publication is very complicated in its structure and preparation, and would therefore not be facile in more extensive technical production. Furthermore, said copolymer and thus prepared membrane contains urea groups and hydrolyzable urethane groups, which are undesirable in long-term medical applications as a possible site for degradation or reaction.

The document U.S. Pat. No. 4,600,751 discloses the manufacturing of an elastomer of the above-mentioned type by crosslinking it in the presence of a monomer, i.e. the monomer functions partly as a crosslinking agent. A part of these monomers polymerize, thus forming micelles of oligomers and polymers in the final elastomer.

OBJECT OF THE INVENTION

The object of the invention is to provide an alternative method for preparing a siloxane-based elastomer composition comprising at least one elastomer, said elastomer composition comprising poly(alkylene oxide) groups present in the elastomer as alkoxy-terminated grafts of polysiloxane units and linked to the polysiloxane units by silicon-carbon bonds, said method providing an elastomer not having the above-mentioned drawbacks, i.e. being free from any impurities and having the desired, predetermined properties.

SUMMARY OF THE INVENTION

The invention thus relates to a method for the preparation of a siloxane-based elastomer composition comprising at least one elastomer, said elastomer composition comprising poly(alkylene oxide) groups present in the elastomer as alkoxy-terminated grafts of polysiloxane units and linked to the polysiloxane units by silicon-carbon bonds wherein at least one vinyl functional polymer component is crosslinked in the presence of a peroxide catalyst.

DETAILED DESCRIPTION OF THE INVENTION

The invention relates to a method as described above. The elastomer composition prepared by said method is used for example as a membrane or matrix for controlling the permeation rate or diffusion rate of a pharmaceutically active drug. Said membrane or matrix may be used for example in intravaginal devices, intrauterine devices, intracervical devices and implants. The pharmaceutically active drug may be for example a hormone such as an antiprogestin, a progestin, an estradiol or an androgen.

General Description of the Elastomer Composition

The term "elastomer composition" may stand for one single elastomer, in which case the polysiloxane units which contain poly(alkylene oxide) groups are present in the said elastomer.

According to another embodiment, the elastomer composition may be made up of two elastomers which are interlaced, one inside the other. In this case the first elastomer comprises poly(alkylene oxide) groups so that the poly(alkylene oxide) groups are present in the said elastomer as alkoxy-terminated grafts of polysiloxane units linked to the polysiloxane units by silicon-carbon bonds. The second elastomer may be a siloxane-based elastomer, suitably a poly(dimethyl siloxane)-based elastomer. The said second elastomer may possibly also comprise poly(alkylene oxide) groups. These poly(alkylene oxide) groups may also be present as alkoxy-terminated grafts of poly(dimethyl siloxane) units linked to the poly(dimethyl siloxane) units by silicon-carbon bonds.

According to a third embodiment, the elastomer composition may be a blend which comprises a siloxane-based elastomer, which is, for example, made up of PDMS, and at least one straight-chain polysiloxane copolymer which comprises poly(alkylene oxide) groups. In this case the poly(alkylene oxide) groups are present in the said polymer as alkoxy-terminated grafts of polysiloxane units linked to the polysiloxane units by silicon-carbon bonds. In this embodiment, also the siloxane-based elastomer may comprise poly(alkylene oxide) groups, in which case these poly(alkylene oxide) groups are present in the elastomer as alkoxy-terminated grafts of polysiloxane units linked to the polysiloxane units by silicon-carbon bonds.

Of course, the elastomer composition may also be made up of two elastomers interlaced one inside the other, as above, and at least one straight-chain polysiloxane copolymer which comprises poly(alkylene oxide) groups.

The poly(alkylene oxide) groups of the elastomer composition may suitably be, for example, poly(ethylene oxide) groups (PEO groups).

The polysiloxane units of the elastomer composition are preferably groups having the formula

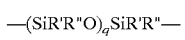

where R' and R" are groups, which are the same or different and which are a lower alkyl group, or a phenyl group, in which case the said alkyl or phenyl groups may be substituted or unsubstituted, or alkoxy-terminated poly(alkylene oxide) groups having the formula

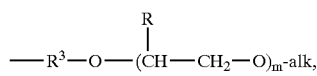

where alk is a lower alkyl group, suitably methyl, R is hydrogen or a lower alkyl, m is 1 ... 30, and R³ is a straight or branched $C_2$–$C_6$ alkyl group, possibly some unreacted groups, such as vinyl or vinyl-terminated alkene, and q is 1 ... 3000.

The term "lower alkyl" stands here and generally in the description of the present invention for $C_1$–$C_6$ alkyl groups.

The above-mentioned free R' and R" groups are suitably a lower alkyl group, preferably methyl.

The term "poly(alkylene oxide) group" means that said group comprises at least two alkyl ether groups successively connected to each other.

The elastomer composition suitably contains a filler, such as silica, in order that the membrane should obtain a sufficient strength.

The word "membrane" means the same as film.

General Description of the Method for the Preparation of the Elastomer Composition According to a preferred embodiment, the elastomer is prepared by crosslinking, in the presence of a peroxide catalyst, at least one vinyl-functional polymer component.

By crosslinking is meant the reaction of the vinyl and methyl groups with each other to form carbon-carbon bonds. A crosslink may also be formed between two methyl groups or between two vinyl groups.

According to the present invention, said peroxide catalyst may be either a non-vinyl specific catalyst or a vinyl specific catalyst. As an example of non-vinyl specific catalyst, dichlorobentsoyl peroxide can be mentioned. On the other hand, 2,5-bis(tert-butylperoxy)-2,5-dimethylhexane, dicumyl peroxide, tert-butyl cumyl peroxide or 2,2-bis(tert-butylperoxy)butane may be used as vinyl specific catalyst. It is also possible to use catalysts that are both vinyl specifics and non-vinyl specifics, such as tert-butyl peroxybenzoate.

According to an embodiment of the invention, the vinyl-functional polymer component comprises a vinyl-functional polysiloxane copolymer having the formula

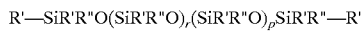

where, in the first block, R' and R" are the same or different and are a lower alkyl group, or a phenyl group, in which case the said alkyl or phenyl group may be substituted or unsubstituted, and where some of the substituents R' and/or R" have been substituted for by vinyl groups, and r is 1 ... 27000, and where, in the second block, R' is a lower alkyl group, or an alkoxy-terminated poly(alkylene oxide) group having the formula

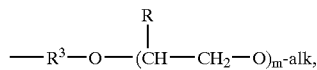

where alk is a lower alkyl group, suitably methyl, R³ is a straight or branched $C_2$–$C_6$ alkyl group, R is hydrogen or a lower alkyl group, and m is 1 ... 30, or R' is a phenyl group, in which case the said alkyl or phenyl group may be substituted or unsubstituted, and R" is a lower alkyl group or a phenyl group, in which case the said alkyl or phenyl group may be substituted or unsubstituted, and p is 1 ... 5000.

The values of r, m and p may be chosen freely within the limits given and a person skilled in the art will be able to choose their values in order to achieve the desired properties.

According to another embodiment, the vinyl functional polymer component further comprises a vinyl-functional polysiloxane having the formula

where R' and R" are the same or different and are a lower alkyl group or a phenyl group, in which case the said alkyl or phenyl group may be substituted or unsubstituted, and where some of the substituents R' and/or R" have been substituted for by vinyl groups, and r is 1 ... 27000.

The vinyl-functional polymer component may contain a filler, suitably silica.

The elastomer composition made up of two elastomers may be prepared so that initially a first elastomer is formed, whereafter a second elastomer is formed by crosslinking in the presence of the first elastomer. Thus the elastomers will form an interpenetrating network (IPN).

EXPERIMENTAL SECTION

Elastomer Compositions Prepared

In the elastomer composition described below peroxide was used as the catalyst for crosslinking, in which case the vinyl or methyl groups reacted, forming carbon-carbon bonds. In a first step, a base polymer blend was prepared, in which case all of the vinyl-containing polymers and the fillers, or vinyl-containing polymers which contained a filler, were mixed together. The filler used was silica.

The elastomer membrane had the following composition: PDMS-PEO graft copolymer together or separately with a siloxane, a polymer that does or does not contain a filler and a crosslinking agent peroxide.

The weighed blend was placed between two fluorinated ethylene-propylene (FEP) release membranes in the center of a round metal form having a thickness of 0.4 mm and an inner diameter of 8 cm. The blend, together with the forms and the FEP membranes, was placed between the compression surfaces of the hot-press, which surfaces had been heated in advance to +115° C. The surfaces were pressed together and were kept pressed at a pressure of 200 bar for 5 minutes. The pressure was released and the membrane was allowed to set at room temperature for 24 hours.

Elastomer Membrane

Ingredients used for the preparation of the elastomer:

PDMS-PEO graft copolymer having a vinyl concentration of 0.0743 mmol/g and a PEO content of 1.28% by weight Dichlorobenzoyl peroxide Perkadox PD50 S, Nusil The PDMS-PEO graft copolymer used was prepared as follows:

600 g of octamethyl cyclotetrasiloxane ($D_4$), 9.28 g of poly(dimethyl siloxane)-poly(ethylene oxide) graft copolymer (Gelest, DBE-821, containing 80% by weight PEO), 6.18 g of dimethyl vinyl silyl end-blocked PDMS (end-blocker, Bayer Silopren U2), and 3.1 g of tetramethyl tetravinyl cyclotetrasiloxane were weighed. The reactor was nitrogenated, the weighed chemicals were poured in, and stirring was started. The inside temperature of the reactor was raised to 135° C., and the catalyst (potassium siloxanolate, 0.9 ml, 20 ppm $K^+$) was added to the reaction solution. The viscosity of the reaction solution began to increase vigorously, and at 1 h from the adding of the catalyst it was possible to deactivate the catalyst by increasing the reactor pressure to 2 bar for a period of 15 minutes by means of carbon dioxide. Thereafter the light cyclic compounds (13% by weight) were removed from the reaction solution by distillation (10 mbar, 30 min, 135° C.). Product $M_n$=190,000 g/mol.

The amounts of the ingredients in the composition example were as follows:

PDMS-PEO graft copolymer 98.8% by weight

Dichlorobenzoyl peroxide Perkadox PD50 S 1.2% by weight 10 grams of the PDMS-PEO graft copolymer and 0.12 grams of Perkadox PD50 S were mixed together. The blend was hardened at a temperature of +115° C. and a pressure of 200 bar for 5 minutes and was cured at +150° C. for 2 hours.

An elastomer composition according to the invention is, for example, highly suited for controlling, in implants and in intrauterine and intravaginal devices, the permeation rates of drugs having hormonal action.

The most important drugs having hormonal action include antiprogestins, progestins, estradiols and androgens.

The above embodiments of the invention are only examples of the implementation of the idea of the invention. For a person skilled in the art it is clear that the different embodiments of the invention may vary within the framework of the claims presented below.

What is claimed is:

1. A method for preparation of a siloxane-based elastomer composition comprising at least one elastomer, said method comprising crosslinking at least a vinyl functional polymer component comprising poly(alkylene oxide) groups in the presence of a peroxide catalyst, said poly(alkylene oxide) groups being present in the elastomer as alkoxy-terminated grafts of polysiloxane units and linked to the polysiloxane units by silicon-carbon bonds.

2. The method of claim 1, wherein said peroxide catalyst is a non-vinyl specific catalyst.

3. The method of claim 2, wherein said non-vinyl specific catalyst is dichlorobenzoyl peroxide.

4. The method of claim 1, wherein said peroxide catalyst is a vinyl specific catalyst.

5. The method of claim 4, wherein said vinyl specific catalyst is selected from the group consisting of 2,5-bis(tert-butylperoxy)-2,5-dimethylhexane, dicumyl peroxide, tert-butyl cumyl peroxide and 2,2-bis(tert-butylperoxy)butane.

6. The method of claim 1, wherein the elastomer consists essentially of polysiloxane units which comprise said poly(alkylene oxide) groups.

7. The method of claim 6, wherein the formula of the polysiloxane unit is

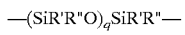

where R' and R" are groups, which are the same or different and which are a lower alkyl group, or a phenyl group, in which case said alkyl or phenyl group may be substituted or unsubstituted, or alkoxy-terminated poly(alkylene oxide) groups having the formula

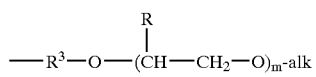

where alk is a lower alkyl group, R is hydrogen or a lower alkyl, $R^3$ is a straight-chain or branched $C_2$–$C_6$ alkylene, and m is 1 to 30, optionally some unreacted groups selected from the group consisting of vinyl and vinyl-terminated alkene, and q is 1 to 3000.

8. The method of claim 7, wherein said alk is methyl.

9. The method of claim 7, wherein the R' and R" groups are a lower alkyl group.

10. The method of claim 9, wherein said lower alkyl group is methyl.

11. The method of claim 1, wherein the vinyl-functional polymer component comprises a vinyl-functional polysiloxane copolymer having the formula

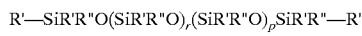

where, in the first block, R' and R" are the same or different and are a lower alkyl group, or a phenyl group, in which case said alkyl or phenyl group may be substituted or unsubstituted, and where some of the substituents R' and/or R" have been substituted for by vinyl groups, and r is 1 to 27000, and where, in the second block, R' is a lower alkyl group, or an alkoxy-terminated poly(alkylene oxide) group having the formula

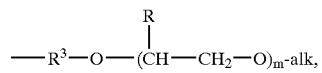

where alk is a lower alkyl group, $R^3$ is a straight or branched $C_2$–$C_6$ alkylene group, R is hydrogen or a lower alkyl group, and m is 1 to 30, or R' is a phenyl group, in which case said alkyl or phenyl group may be substituted or unsubstituted, and R" is a lower alkyl group or a phenyl group, in which case said alkyl or phenyl group may be substituted or unsubstituted, and p is 1 to 5000.

12. The method of claim 11, wherein alk is methyl.

13. The method of claim 11, wherein the vinyl functional polymer component further comprises a vinyl-functional polysiloxane having the formula

where R' and R" are the same or different and are a lower alkyl group or a phenyl group, in which case said alkyl or phenyl group may be substituted or unsubstituted, and where some of the substituents R' and/or R" have been substituted for by vinyl groups, and r is 1 to 27000.

14. The method of claim 1, wherein the vinyl-functional polymer component contains a filler.

15. The method of claim 14, wherein said filler comprises silica.

16. The method of claim 1, wherein the elastomer composition further comprises a non-crosslinked polymer.

17. The method of claim 1, wherein the poly(alkylene oxide) groups are poly(ethylene oxide) groups.

* * * * *